US010921302B2

(12) United States Patent
Noh et al.

(10) Patent No.: US 10,921,302 B2
(45) Date of Patent: Feb. 16, 2021

(54) METHOD FOR MANUFACTURING CHEMOCHROMIC NANOPARTICLES

(71) Applicants: Hyundai Motor Company, Seoul (KR); Kia Motors Corporation, Seoul (KR); Ajou University Industry-Academic Cooperation Foundation, Gyeonggi-do (KR)

(72) Inventors: Yong Gyu Noh, Gyeonggi-do (KR); Hyun Joon Lee, Gyeonggi-do (KR); Hyo Sub Shim, Gyeonggi-do (KR); Hyung Tak Seo, Seoul (KR); Yeong An Lee, Gyeongsangnam-do (KR); Shankara S. Kalanur, Gyeonggi-do (KR)

(73) Assignees: Hyundai Motor Company, Seoul (KR); Kia Motors Corporation, Seoul (KR); Ajou University Industry-Academic Cooperation Foundation, Gyeonggi-do (KR)

( * ) Notice: Subject to any disclaimer, the term of this patent is extended or adjusted under 35 U.S.C. 154(b) by 0 days.

(21) Appl. No.: 16/508,930

(22) Filed: Jul. 11, 2019

(65) Prior Publication Data
US 2019/0339239 A1    Nov. 7, 2019

Related U.S. Application Data

(62) Division of application No. 15/138,325, filed on Apr. 26, 2016, now abandoned.

(30) Foreign Application Priority Data

Sep. 1, 2015 (KR) .......................... 10-2015-0123830

(51) Int. Cl.
*B05D 3/06* (2006.01)
*G01N 21/78* (2006.01)
(Continued)

(52) U.S. Cl.
CPC ............ *G01N 33/005* (2013.01); *B01J 23/30* (2013.01); *B01J 23/44* (2013.01); *B01J 23/58* (2013.01);
(Continued)

(58) Field of Classification Search
CPC ............ G01N 33/005; F01N 2560/024; B01J 37/345; B05D 3/061; B05D 3/065; B05D 3/067
See application file for complete search history.

(56) References Cited

U.S. PATENT DOCUMENTS 4,264,421 A * 4/1981 Bard ..................... B01J 23/40
                                            204/157.51
4,579,751 A * 4/1986 Forster ................. G01N 27/125
                                            338/34
(Continued)

FOREIGN PATENT DOCUMENTS

CN     101898129 A     12/2010
CN     103140974 A     6/2013
(Continued)

OTHER PUBLICATIONS

Kalanur, S.S. et al. "Green deposition of Pd nanoparticles on WO3 for optical, electronic and gasochromic hydrogen sensing applications," Sensors and Actuators B 221 (2015) 411-417; Available online Jun. 28, 2015 (Year: 2015).*
(Continued)

*Primary Examiner* — Christopher Adam Hixson
*Assistant Examiner* — Michelle Adams
(74) *Attorney, Agent, or Firm* — Mintz Levin Cohn Ferris Glovsky; Peter F. Corless

(57) ABSTRACT

Disclosed are a chemochromic nanoparticle, a method for manufacturing the chemochromic nanoparticle, and a hydrogen sensor comprising the chemochromic nanoparticle. In
(Continued)

particular, the chemochromic nanoparticle has a core-shell structure such that the chemochromic nanoparticle and comprises a core comprising a hydrated or non-hydrated transition metal oxide; and a shell comprising a transition metal catalyst.

4 Claims, 7 Drawing Sheets

(51) Int. Cl.
| | | |
|---|---|---|
| B01J 37/34 | (2006.01) | |
| G01N 33/00 | (2006.01) | |
| G01N 27/04 | (2006.01) | |
| C01G 41/02 | (2006.01) | |
| B01J 35/00 | (2006.01) | |
| B01J 23/30 | (2006.01) | |
| B01J 23/652 | (2006.01) | |
| B01J 23/44 | (2006.01) | |
| B01J 23/60 | (2006.01) | |
| B01J 35/02 | (2006.01) | |
| B01J 23/648 | (2006.01) | |
| B01J 23/58 | (2006.01) | |
| B01J 23/89 | (2006.01) | |
| B01J 37/03 | (2006.01) | |
| B01J 23/62 | (2006.01) | |
| B05D 5/06 | (2006.01) | |

(52) U.S. Cl.
CPC ............. *B01J 23/60* (2013.01); *B01J 23/62* (2013.01); *B01J 23/626* (2013.01); *B01J 23/6482* (2013.01); *B01J 23/6525* (2013.01); *B01J 23/6527* (2013.01); *B01J 23/892* (2013.01); *B01J 23/8906* (2013.01); *B01J 23/8926* (2013.01); *B01J 35/002* (2013.01); *B01J 35/008* (2013.01); *B01J 35/023* (2013.01); *B01J 37/035* (2013.01); *B01J 37/34* (2013.01); *B01J 37/343* (2013.01); *B01J 37/345* (2013.01); *C01G 41/02* (2013.01); *G01N 21/783* (2013.01); *G01N 27/04* (2013.01); *B05D 3/067* (2013.01); *B05D 5/065* (2013.01); *C01P 2006/40* (2013.01); *F01N 2560/024* (2013.01)

(56) References Cited

U.S. PATENT DOCUMENTS

| | | | |
|---|---|---|---|
| 6,535,658 | B1 | 3/2003 | Mendoza et al. |
| 7,910,373 | B2 | 3/2011 | Liu et al. |
| 8,003,055 | B1 | 8/2011 | Muradov |
| 8,048,384 | B1 | 11/2011 | Bokerman et al. |
| 10,094,811 | B2 * | 10/2018 | Noh .................... G01N 31/10 |
| 2005/0025700 | A1 | 2/2005 | Bulian et al. |
| 2007/0251822 | A1 | 11/2007 | Hoagland et al. |
| 2009/0267032 | A1 | 10/2009 | Takano et al. |
| 2010/0297447 | A1 * | 11/2010 | Tadakuma ............... B01J 23/14 428/403 |
| 2010/0304954 | A1 * | 12/2010 | Sogabe .................. B01J 21/063 502/5 |
| 2011/0171066 | A1 | 7/2011 | Captain et al. |
| 2013/0004372 | A1 | 1/2013 | Roberson et al. |
| 2014/0004444 | A1 | 1/2014 | Cerri et al. |
| 2014/0193746 | A1 | 7/2014 | Cerri et al. |
| 2016/0367968 | A1 * | 12/2016 | Guerrero ................ B01J 37/345 |

FOREIGN PATENT DOCUMENTS

| | | | | |
|---|---|---|---|---|
| CN | 103420424 | A | | 12/2013 |
| JP | H05107241 | A | | 4/1993 |
| JP | 2005-174869 | A | | 6/2005 |
| JP | 2005-270864 | A | | 10/2005 |
| JP | 2005-345338 | A | | 12/2005 |
| JP | 2006-292451 | A | | 10/2006 |
| JP | 2007-278744 | A | | 10/2007 |
| JP | 2013-540998 | A | | 11/2013 |
| KR | 2009-0115324 | A | | 11/2009 |
| KR | 10-2012-0070160 | A | | 6/2012 |
| KR | 101557611 | B1 * | 10/2015 | ............. G01N 33/28 |
| WO | WO-2015059503 | A1 * | 4/2015 | ............. B01J 27/24 |

OTHER PUBLICATIONS

Tahmasebi, N. et al. "Synthesis and optical properties of Au decorated colloidal tungsten oxide nanoparticles," Applied Surface Science 355 (2015) 884-890; Available online Jul. 29, 2015 (Year: 2015).*

Ranjbar, M. "Gasochromic effect in colloidal nanoparticles of tungsten oxide dihydrate synthesized via a simple anodizing method," Solar Energy Materials & Solar Cells 132 (2015) 329-336; Available online Sep. 30, 2014 (Year: 2014).*

Delalat, F. et al. "Blue colloidal nanoparticles of molybdenum oxide by simple anodizing method: decolorization by PdCl2 and observation of in-liquid gasochromic coloration," Solar Energy Materials & Solar Cells 144 (2016) 165-172; Available online Sep. 19, 2015 (Year: 2015).*

Garavand, N.T. et al. "Pd2+ reduction and gasochromic properties of colloidal tungsten oxide nanoparticles synthesized by pulsed laser ablation," Appl Phys A (2012) 108:401-407 (Year: 2012).*

Mirzaei, A. et al. "Gasochromic WO3 Nanostructures for the Detection of Hydrogen Gas: An Overview," Appl. Sci. 2019, 9, 1775, 1-21 (Year: 2019).*

Office Action dated Sep. 27, 2019 in corresponding Chinese Application No. 201610320113.9.

Garavand et al., "Colouration process of colloidal tungsten oxide naoparticles in the presence of hydrogen gas", Applied Surface Science, vol. 258, pp. 10089-10094 (2012).

Garavand, N. T. et al, "Colouration process of colloidal tungsten oxide nanoparticles in the presence of hydrogen gas", Applied Surface Science, 258 (2012) pp. 10089-10094.

Extended European Search Report for European Patent Application No. 16168950.0, dated Dec. 6, 2016, 9 pages.

Kalanur, S. et al., "Eye-readable gasochromic and optical hydrogen gas sensor based on CuS—Pd", RSC Advances, Issue 12, (2015) pp. 9029-9034.

Sekimoto, S. et al, "A fiber-optic evanescent-wave hydrogen gas sensor using palladium-supported tungsten oxide", Sensors and Actuators B, 66 (2000) pp. 142-145.

Li, et al., "Preparation of Nano-sized WO3 by H2O2 Oxidation Hydrothermal Crystallization Combined Method", Chinese Journal of Rare Metals, Jun. 2005, 29(3):377-380. (English Abstract attached).

* cited by examiner

METHOD FOR MANUFACTURING CHEMOCHROMIC NANOPARTICLES

CROSS-REFERENCE TO RELATED APPLICATION

This application is a Divisional of U.S. application Ser. No. 15/138,325, filed on Apr. 26, 2016, which is based on and claims the benefit of Korean Patent Application No. 10-2015-0123830, filed on Sep. 1, 2015 in the Korean Intellectual Property Office, the disclosure of which is incorporated herein in its entirety by reference.

TECHNICAL FIELD

The present invention relates to a chemochromic nanoparticle, a method for manufacturing the chemochromic nanoparticle, and a hydrogen sensor comprising the chemochromic nanoparticle. In particular, the chemochromic nanoparticle may have a core-shell structure comprising a core of a hydrated or non-hydrated transition metal oxide and a shell of a metal catalyst.

BACKGROUND

Hydrogen fuel energy does not cause environmental contamination and may be infinitely recyclable. Accordingly, the hydrogen fuel energy has been newly spotlighted as a new generation energy source capable of replacing petroleum energy. Therefore, recently, research for storing and controlling the hydrogen fuel energy has been actively conducted in various fields such as production technologies, storage technologies, transportation and movement technologies, and the like. Particularly, research into a hydrogen fuel cell vehicle using the hydrogen fuel energy has been most prominent.

However, hydrogen is combustible gas and having a risk of ignition and explosion when a concentration of hydrogen in the air is 4% or greater. Therefore, it is essential to strictly manage and supervise hydrogen gas in all of the technical fields using the hydrogen fuel energy. Among them, a core technology for commercializing the hydrogen fuel energy may be implementing a highly sensitive method for detecting hydrogen such that leakage of hydrogen gas may be rapidly and accurately detected.

According to the related art, electric sensor devices detecting hydrogen gas using the principles associated with electrochemical, mechanical, acoustic, thermal conductivity, and resistance changes and work functions have been used. However, because these electric sensors detect the presence or absence of leakage of hydrogen gas through a change in electrical resistance, a package including a power supply part is required, such that most of the sensors are not suitable for being used on a large scale due to expensive cost, a large size, a complicated structure, and low selectivity. In addition, since the sensors are used in an electric environment in which the sensor may be exploded at the time of detection operation, the sensors have a disadvantage of high risk.

Recently, in order to overcome the disadvantages as described above, a sensor using a method for chemically detecting hydrogen gas using a material bleached or discolored when the material is exposed to hydrogen has been suggested.

As a representative example of the material that can be discolored in exposure to hydrogen, a transition metal oxide has been known as a representative electrochromic material of which a color is changed in the case of configuring an electrochemical cell and applying an electric field thereto. Typically, change in color of the transition metal oxide is caused by a change in electronic structure due to electrochemical oxidation or reduction of a transition metal when cations and electrons are injected.

Meanwhile, since hydrogen hardly reacts with a metal material or semiconductor material, in order to solve this problem, a metal catalyst, or the like, that may facilitate or induce a reaction with hydrogen may be coated on the transition metal oxide, such that reactivity with hydrogen may be significantly increased.

As illustrated in FIG. 1, when hydrogen molecules in hydrogen gas are dissociated into hydrogen ions (protons) and electronics by the metal catalyst, and the hydrogen ion pass through a metal catalyst layer to thereby be injected into a transition metal oxide layer comprising the electrochromic material below the metal catalyst layer by diffusion, a color of the transition metal oxide can be changed (see the following Reaction Formula 1). In this case, the presence or absence of hydrogen gas may be detected by measuring transmittance of a thin film to monitor a change in color. A phenomenon that the color of the thin film is changed by gas is referred to as gasochromism.

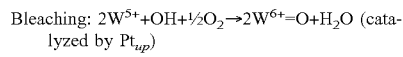

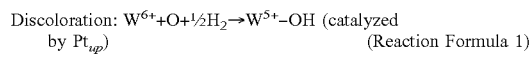
(Reaction Formula 1)

The sensor using the method for chemically detecting hydrogen gas as described above has advantages, for example, long-distance detection using a cable may be performed, the sensor may be repetitively used due to reversible change in color, and the sensor does not require an additional electric circuit in a detection region to thereby have high safety.

However, when the sensor is used for chemically detecting hydrogen, since a sputtering method, a vapor deposition method, or the like, in which high pressure is applied is used in order to closely attach and adhere the metal catalyst to a surface of a substrate (or the transition metal oxide). As such, bonding strength between the metal catalyst layer and the transition metal oxide layer may be increased, such that sensitivity with respect to hydrogen gas may be decreased. Further, in the case in which metal catalyst particles are not closely attached to the substrate, when the metal catalyst particles are exposed to hydrogen gas, a lattice of the metal catalyst particles may be expanded, but when exposure to hydrogen gas is stopped, the lattice may not recovered in an initial state, such that reproducibility may be decreased.

As described above, the hydrogen sensors according to the related art may not be alternatives to the existing sensors in view of detection capability, sensitivity, safety, a rapid response time at a low concentration, and the like.

Therefore, a technology of manufacturing a high performance, high life time, and high safety hydrogen detection sensor, capable of being widely used over various industries, enabling visual identification by using a hydrogen detection method, may have excellent convenience in view of cost and a manufacturing process, and does not cause a decrease in sensitivity, has been required.

SUMMARY

In preferred aspects, the present invention provides a chemochromic nanoparticle having a core-shell structure and having substantially improved sensitivity and selectivity to hydrogen. The term "chemochromic" or "chemochromic material" as used herein refers to a material or compound that may change in color, transmission/reflection properties, or optical properties. The chemochromic material or compound may chemically react such that the color, transmission/reflection properties, or optical properties may be changed between before the reaction and after the reaction, for example, electrochemical oxidation or reduction of a transition metal or transition metal compound. Changes in color, transmission or reflection properties, or optical properties may be evaluated by, for example, a naked eye, a spectrophotometer, a photodetector that converts light or optical signals into electrical signals (impulses) or the like.

In addition, the present invention provides a method for manufacturing the chemochromic nanoparticle with a core-shell structure, and the method may be a simple manufacturing method for the chemochromic nanoparticle as described above. Moreover, the present invention provides a hydrogen sensor which may visually identify and have convenience in view of cost and a manufacturing process by containing the chemochromic nanoparticle with a core-shell structure.

According to an exemplary embodiment of the present invention, a chemochromic nanoparticle may have a core-shell structure. Accordingly, the chemochromic nanoparticle may comprise: a core comprising a hydrated or non-hydrated transition metal oxide; and a shell comprising a metal catalyst. The shell may be entirely or partially coated on a surface of the core.

The transition metal oxide may comprise a non-hydrated transition metal oxide which is not doped with water molecules or a hydrated transition metal oxide which is doped with water molecules.

The transition metal oxide may comprise a metal oxide of one or two or more selected from the group consisting of $SnO_2$, $TiO_2$, $ZnO$, $VO_2$, $In_2O_3$, $NiO$, $MoO_3$, $SrTiO_3$, $Fe_2O_3$, $WO_3$, and $CuO$.

The transition metal oxide may preferably comprise tungsten oxide ($WO_3$).

An average particle size of the transition metal oxide may suitably range from about 1 to about 200 nm.

The metal catalyst may suitably comprise one metal or particles of two or more metals selected from the group consisting of Pd, Pt, Ru, Mg, Au, and Ir.

The metal catalyst may comprise one or two or more metal compounds selected from the group consisting of palladium chloride ($PdCl_2$), palladium ammonium nitrate ($Pd(NH_3)_2(NO_3)$), palladium bromide ($PdBr_2$), palladium oxide hydrate ($PdOH_2O$), palladium sulfate ($PdSO_4$), palladium nitrate ($Pd(NO_3)_2$), palladium acetylacetate (($CH_3COCH=C(O^-)CH_3)_3Pd$), platinum chloride ($PtCl_2$, $PtCl_4$), platinum bromide ($PtBr_2$), platinum oxide ($PtZO_{2x}H_2O$), platinum sulfide ($PtS_2$), ruthenium oxide hydrate ($RuO_{2x}H_2O$), ruthenium acetylacetate [($CH_3COCH=C(O^-)CH_3)_3Ru$], ruthenium bromide ($RuBr_3$), iridium chloride ($IrCl_3$), iridium acetylacetate (($CH_3COCH=C(O^-)CH_3)_3Ir$), and iridium chloride hydrate ($IrCl_{4x}H_2O$).

The metal catalyst may preferably comprise palladium chloride ($PdCl_2$).

The shell comprising the metal catalyst may be formed using a solution synthesis method using UV irradiation.

A thickness of the shell comprising the metal catalyst may suitably range from about 0.1 to about 50 nm.

Preferably, the shell may be partially coated on the surface of the core in a dot form.

The term "partially coated" as used herein means being coated in a portion of a total surface area, for example, of about 10% or less, of about 20% or less, of about 30% or less, of about 40% or less, of about 50% or less, of about 60% or less, of about 70% or less, of about 80% or less, of about 90% or less, or of about 95% or less of the total surface area. For example, the shell of the nanoparticle may be coated on about 10% or less, of about 20% or less, of about 30% or less, of about 40% or less, of about 50% or less, of about 60% or less, of about 70% or less, of about 80% or less, of about 90% or less, or of about 95% or less of the total surface area of the core.

In a preferred aspect, the chemochromic nanoparticle may comprise: the cored in an amount of about 80 to 90 wt % and the shell in an amount of about 10 to 20 wt % based on the total weight of the chemochromic nanoparticle.

According to an exemplary embodiment of the present invention, a method for manufacturing a chemochromic nanoparticle having a core-shell structure may comprise: preparing a hydrated or non-hydrated transition metal oxide; preparing a metal catalyst solution by dissolving a metal catalyst precursor and a polymer compound in an organic solvent; preparing a mixed solution by injecting the hydrated or non-hydrated transition metal oxide into the metal catalyst solution; manufacturing a chemochromic nanoparticle with a core-shell structure by irradiating UV light to the mixed solution; and obtaining the chemochromic nanoparticle with a core-shell structure by filtering the mixed solution.

The polymer compound may suitably comprise one or a mixture of two or more selected from the group consisting of polyurethane, polyetherurethane, cellulose acetate, cellulose acetate butyrate, cellulose acetate propionate, polymethylmethacrylate (PMMA), polymethylacrylate (PMA), polyacrylic copolymers, polyvinylacetate (PVAc), polyvinylacetate copolymers, polyvinylalcohol (PVA), polystyrene, polystyrene copolymers, polyethyleneoxide (PEO), polypropyleneoxide (PPO), polyethyleneoxide copolymers, polycarbonate (PC), polyvinylchloride (PVC), polycaprolactone, polyvinylpyrrolidone (PVP), polyvinylfluoride, polyvinylidene fluoride copolymers, and polyamide.

The organic solvent suitably may comprise an alcohol based solvent such as methanol or ethanol.

The irradiating of the UV light may suitably be performed by exposure to the UV light having a wavelength of about 365 nm at room temperature for about 2 to 3 minutes, and an output of the UV light may be about 1000 W.

The present invention also provides a method for preparing the hydrated or non-hydrated tungsten oxide. The method may comprise: preparing an aqueous ammonium paratungstate solution; adding hydrochloric acid to the aqueous ammonium paratungstate solution and stirring the mixture to prepare an aqueous tungstic acid solution; adding hydrogen peroxide to the aqueous tungstic acid solution to prepare an aqueous peroxo-polytungstic acid solution; injecting the aqueous peroxo-polytungstic acid solution into an autoclave and performing primary heat treatment; precipitating a hydrated tungsten oxide by air-cooling the autoclave after a reaction is terminated; and obtaining the tungsten oxide.

In one specifically preferred system, the primary heat treatment may be performed at a temperature of about 160° C. in the autoclave and an internal pressure in the autoclave is maintained at about 35 to 50 bar.

The method may further comprise: re-injecting the obtained tungsten oxide into the autoclave; and performing a secondary heat treatment to the tungsten oxide in the autoclave at a temperature of about 500° C.

Further provided is a hydrogen sensor that may comprise the chemochromic nanoparticle with a core-shell structure as described herein.

Still further provided is a vehicle that may comprises a hydrogen sensor comprising the chemochromic nanoparticle as described herein. Other aspects of the present invention are disclosed infra.

BRIEF DESCRIPTION OF THE DRAWINGS

The above and other objects, features and advantages of the present invention will be more apparent from the following detailed description taken in conjunction with the accompanying drawings.

Figure 4:
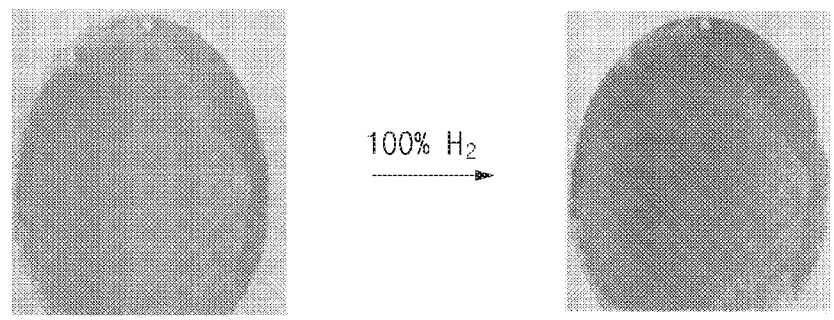

Left side image in FIG. 4 illustrates a result of an exemplary hydrogen sensor containing an exemplary non-hydrated transition metal oxide from Experimental Example 1 according to an exemplary embodiment of the present invention before hydrogen gasochromic test.

Right side image in FIG. 4 illustrates a result of an exemplary hydrogen sensor containing an exemplary non-hydrated transition metal oxide from Experimental Example 1 according to an exemplary embodiment of the present invention after hydrogen gasochromic test. Left side image in FIG. 5 illustrates a result of an exemplary hydrogen sensor comprising an exemplary hydrated transition metal oxide from Experimental Example 1 according to an exemplary embodiment of the present invention before a hydrogen gasochromic test.

Figure 5:
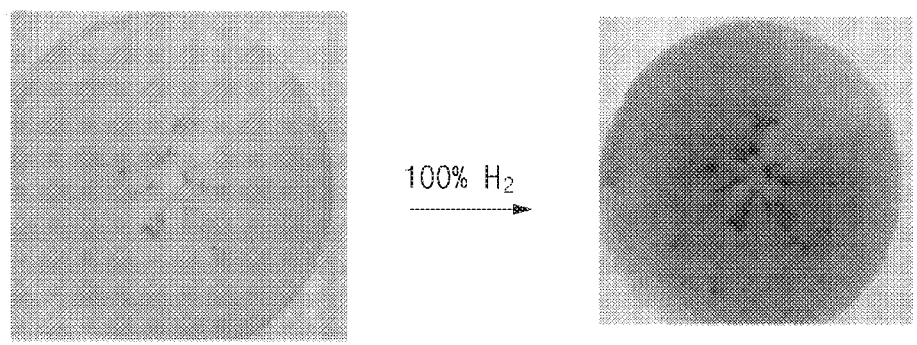

Right side image in FIG. 5 illustrates a result of an exemplary hydrogen sensor comprising an exemplary hydrated transition metal oxide from Experimental Example 1 according to an exemplary embodiment of the present invention after a hydrogen gasochromic test.

Figure 6:
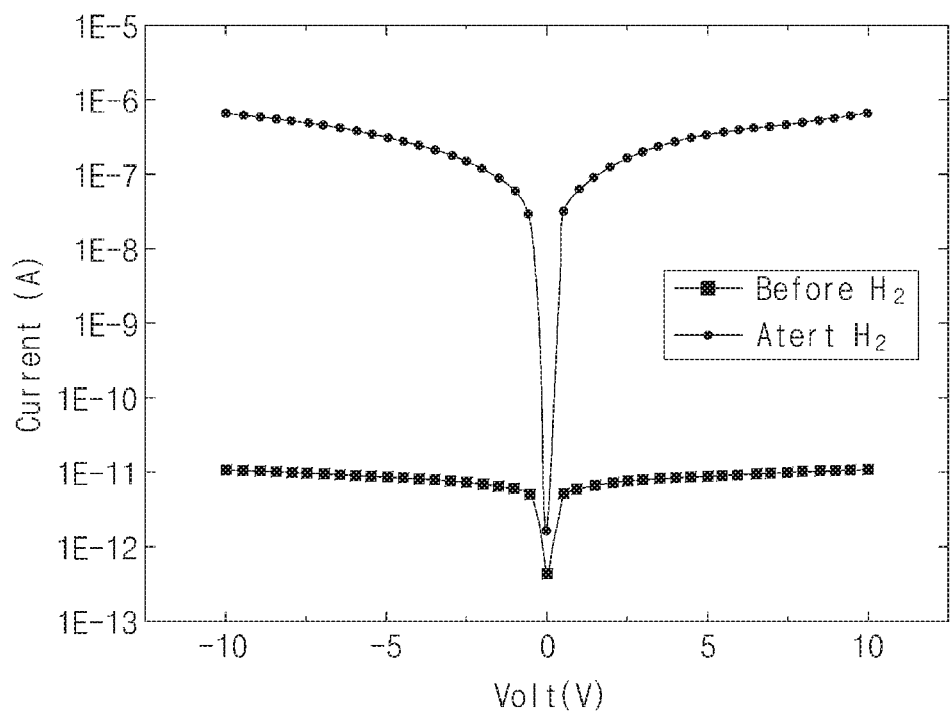

FIG. 6 is a graph illustrating voltage-current response results of an exemplary hydrogen sensor containing an exemplary non-hydrated transition metal oxide from Experimental Example 2 according to an exemplary embodiment of the present invention.

Figure 7:
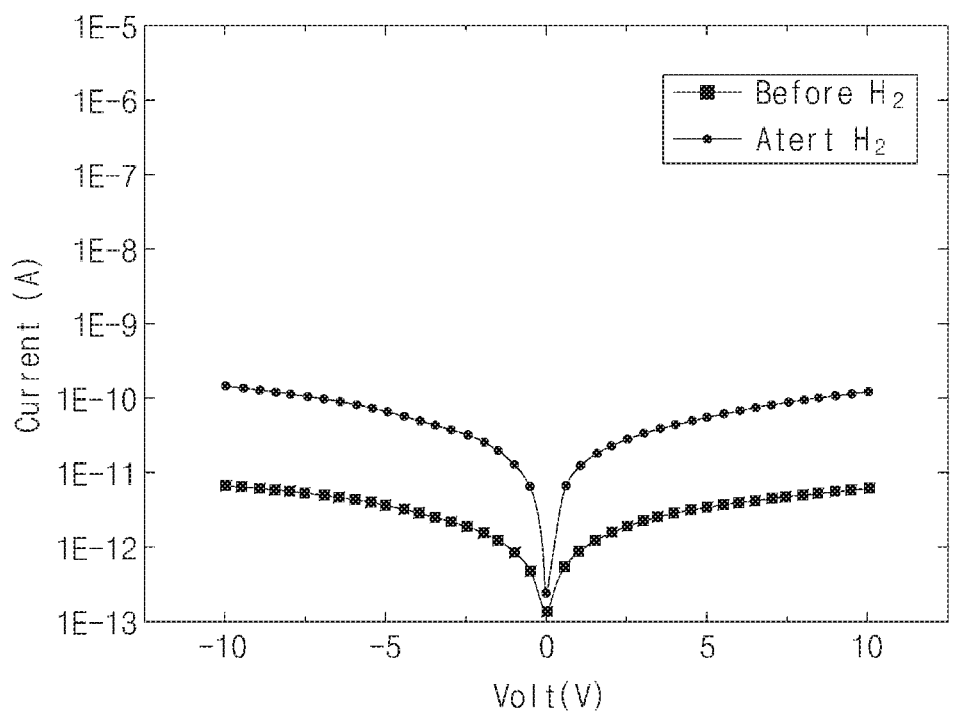

FIG. 7 is a graph illustrating voltage-current response results of an exemplary hydrogen sensor containing an exemplary hydrated transition metal oxide from Experimental Example 2 according to an exemplary embodiment of the present invention.

DETAILED DESCRIPTION

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

Hereinafter, the present invention will be described in detail. Terms and words used in the present specification and claims are not to be construed as a general or dictionary meaning but are to be construed as meaning and concepts meeting the technical ideas of the present invention based on a principle that the inventors can appropriately define the concepts of terms in order to describe their own inventions in best mode.

In detail, according to an exemplary embodiment of the present invention, provided is a chemochromic nanoparticle that may have a core-shell structure, such that the chemochromic nanoparticle may comprise a core comprising a hydrated or non-hydrated transition metal oxide; and a shell comprising a metal catalyst partially coated on a surface of the core. Preferably, the shell maybe entirely or partially coated on the surface of the core. For example, the shell may be coated on about 10%, 20%, 30%, 40%, 50%, 60%, 70%, 80%, 90%, 95% or 99% of the total surface area of the core.

The transition metal oxide for the cored of the nanoparticle may be a material of which a color may be chemically changed due to reduction by a reaction with hydrogen molecules when the material is exposed to hydrogen gas. Representative examples thereof may include a metal oxide of one or two or more selected from the group consisting of $SnO_2$, $TiO_2$, $ZnO$, $VO_2$, $In_2O_3$, $NiO$, $MoO_3$, $SrTiO_3$, $Fe_2O_3$, $WO_3$, and $CuO$. Preferably, the transition metal oxide may be tungsten oxide ($WO_3$).

The transition metal oxide may comprise particles that are not doped with water molecules, that is, non-hydrated particles, in order to be applied to a resistance type sensor. Alternatively, the transition metal oxide may comprise a water molecule-doped hydrated transition metal oxide in order to further improve chemochromic sensitivity.

As an internal structure of the hydrated transition metal oxide is changed due to the water molecules, a diffusion speed of hydrogen molecules may be improved, such that the hydrated transition metal oxide may provide an advantage, for example, color change performance thereof may be substantially improved. On the contrary, the color change performance of the non-hydrated transition metal oxide may not be sufficient, but electric responsibility of the non-hydrated transition metal oxide for hydrogen may be significantly increased, such that the non-hydrated transition metal oxide may also be used as a material of the resistance type sensor.

The term "color change", as used herein, refers to a chemical or optical discoloration that may be visibly observed by naked eyes. In preferred embodiment, the "color change" may refer to a change in visibly detectable colors which is induced by chemical reaction such as reduction, oxidation and the like, with the hydrogen. That is, there would be a visible color change (as detected with naked eyes) of the metal oxide layer between 1) before the metal oxide layer is exposed to the hydrogen; and 2) at least about 1 second, about 5 seconds, about 10 seconds, about 20 seconds, about 30 seconds, about 40 seconds, about 50 seconds, or about 60 seconds after the metal oxide layer is exposed to the hydrogen. Further, the "color change" may be visibly detected with naked eyes when the discoloration material in the metal oxide layer in an amount of about 1 wt %, about 2%, about 3 wt %, about 4 wt %, about 5 wt %, about 7 wt %, about 10 wt %, about 15 wt %, about 20 wt %, about 25 wt %, about 30 wt %, about 35 wt %, about 40 wt %, about 50 wt %, about 60 wt %, about 70 wt %, about 80 wt %, about 90 wt %, about 99 wt %, or about 100 wt % based on the total weight thereof is chemically reacted with the hydrogen.

In the nanoparticle with a core-shell structure according to the present invention, an average particle size of the core comprising the transition metal oxide may range from about 1 to 200 nm, or particularly of about 1 to 100 nm.

Further, in the nanoparticle with a core-shell structure according to the present invention, the metal catalyst may cause a decomposition reaction of the hydrogen molecules. For example, the metal catalyst as used herein may include one metal or mixed particles of two or more metals selected from the group consisting of Pd, Pt, Ru, Mg, Au, and Ir, more specifically, one or two or more metal catalysts selected from the group consisting of palladium chloride ($PdCl_2$), palladium ammonium nitrate ($Pd(NH_3)_2(NO_3)$), palladium bromide ($PdBr_2$), palladium oxide hydrate ($PdOH_2O$), palladium sulfate ($PdSO_4$), palladium nitrate ($Pd(NO_3)_2$), palladium acetylacetate (($CH_3COCH=C(O^-)CH_3)_3Pd$), platinum chloride ($PtCl_2$, $PtCl_4$), platinum bromide ($PtBr_2$), platinum oxide ($PtO_{2x}H_2O$), platinum sulfide ($PtS_2$), ruthenium oxide hydrate ($RuO_{2x}H_2O$), ruthenium acetylacetate [($CH_3COCH=C(O^-)CH_3)_3Ru$], ruthenium bromide ($RuBr_3$), iridium chloride ($IrCl_3$), iridium acetylacetate (($CH_3COCH=C(O^-)CH_3)_3Ir$), and iridium chloride hydrate ($IrCl_{4x}H_2O$). Among them, palladium chloride ($PdCl_2$) containing palladium (Pd) metal particles, which may increase sensitivity in addition to significantly improving durability of a hydrogen sensor, may be preferably used.

The shell comprising the metal catalyst may be uniformly coated by a solution synthesis method using UV irradiation instead of a general chemical bath deposition (CBD) method, dry deposition method, or sputtering method. Therefore, inherent specific physical properties of surfaces of the transition metal oxide particles may be secured.

In addition, the chemochromic nanoparticle with a core-shell structure according to the present invention may include: the core comprising the hydrated or non-hydrated transition metal oxide in an amount of about 80 to 90 wt %; and the shell comprising the metal catalyst in an amount of about 10 to 20 wt %, based on the total weight of the chemochromic nanoparticle.

When the content ratio of the core comprising the transition metal oxide is greater than about 90 wt %, an amount of the metal catalyst adsorbed in the transition metal oxide may be rapidly decreased, such that hydrogen molecule decomposition efficiency may be decreased. In addition, when the content ratio of the transition metal oxide is less than about 80 wt %, change of the color to exposure to hydrogen may not be sufficiently implemented.

A thickness of the shell comprising the metal catalyst may range from about 0.1 to about 50 nm, or particularly from about 1 to about 30 nm. When the coating thickness of the shell is less than about 0.1 nm, capability of dissociating hydrogen molecules may be deteriorated. Preferably, the thickness of the shell may be less than a diameter of the core.

Further, in order to increase sensitivity efficiency of the transition metal oxide with respect to hydrogen gas, the shell may be partially coated on the surface of the core in a dot form instead of being coated on an entire surface of the core comprising the transition metal oxide. For example, a coating area of the shell may be of about 80% or less of the entire surface area of the core. When the coating area of the shell is greater than about 80%, since the shell is coated on the surface of the transition metal in a film form instead of the dot form, a surface area of the metal catalyst contacting hydrogen may be decreased, thereby decreasing capability of decomposing hydrogen.

As described above, in the nanoparticles with a core-shell structure according to the present invention, when the average particle size of the core comprising the transition metal oxide, an average thickness and coating area of the shell comprising the metal catalyst, and the content ratio of the core and shell are all within the above-mentioned ranges, the shell comprising the metal catalyst may be distributed to a uniform thickness on the surface of the core comprising the transition metal oxide. Therefore, a hydrogen sensor having high sensitivity may be manufactured.

In addition, provided is a method for manufacturing a chemochromic nanoparticle with a core-shell structure. The method may comprise: preparing a hydrated or non-hydrated transition metal oxide; preparing a metal catalyst solution by dissolving a metal catalyst precursor and a polymer compound in an organic solvent; preparing a mixed solution by adding the hydrated or non-hydrated transition metal oxide to the metal catalyst solution; manufacturing the chemochromic nanoparticle by irradiating UV light to the mixed solution; and obtaining the chemochromic nanoparticle by filtering the mixed solution. Accordingly, the thus formed chemochromic nanoparticle may be formed to have a core-shell structure.

Hereinafter, the method for manufacturing the chemochromic nanoparticle with a core-shell structure according to the present invention will be described in detail with reference to the accompanying drawings.

Figure 1:
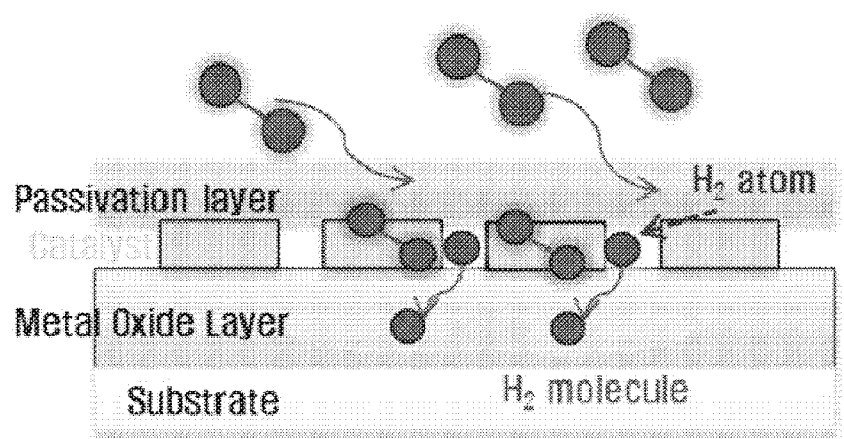
FIG. 1 illustrates an exemplary hydrogen sensor in the related arts.
Figure 2:
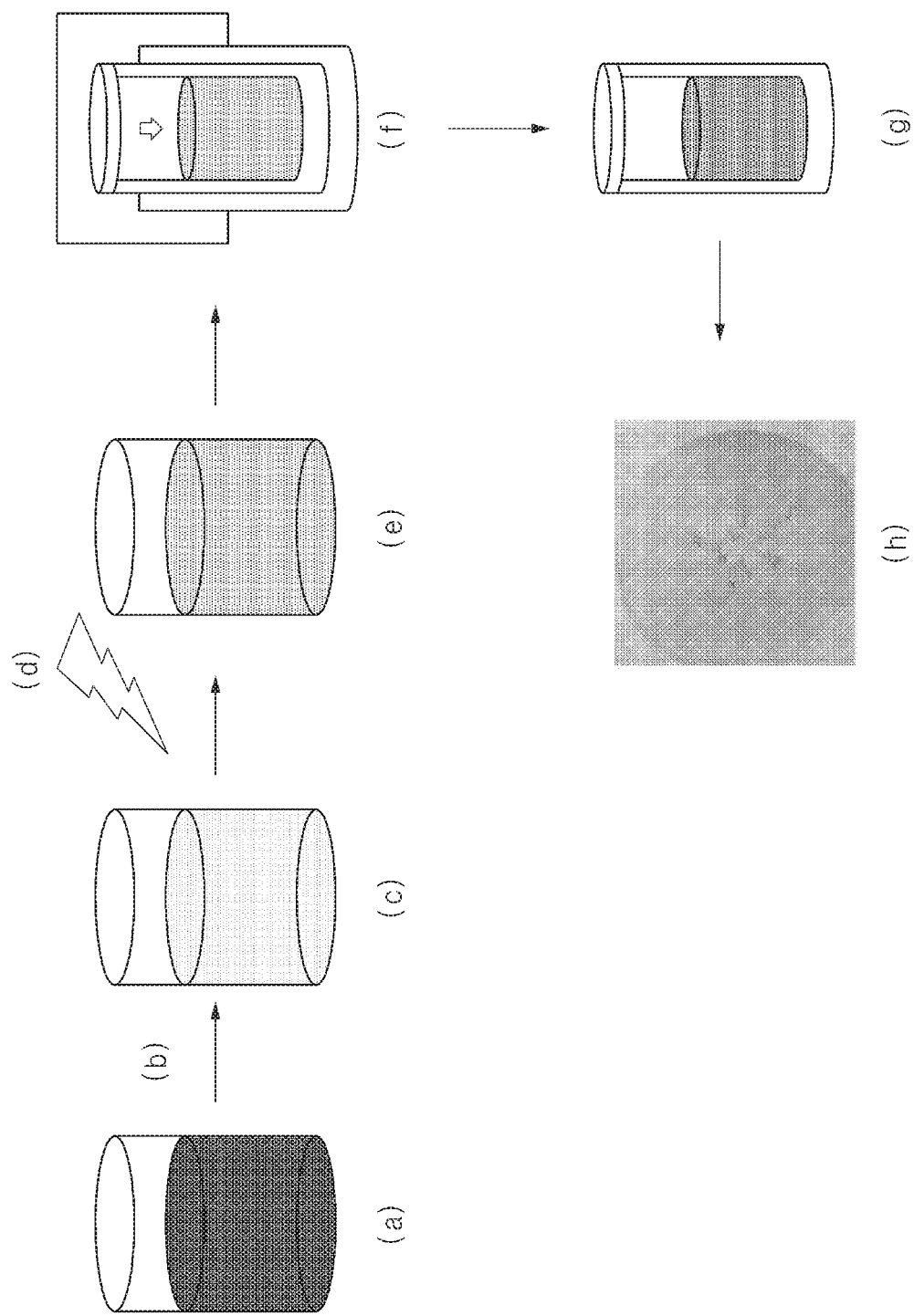
FIG. 2 illustrates an exemplary method for preparing a hydrated or non-hydrated transition metal oxide of Preparation Example 1 according to an exemplary embodiment of the present invention.
Figure 3:
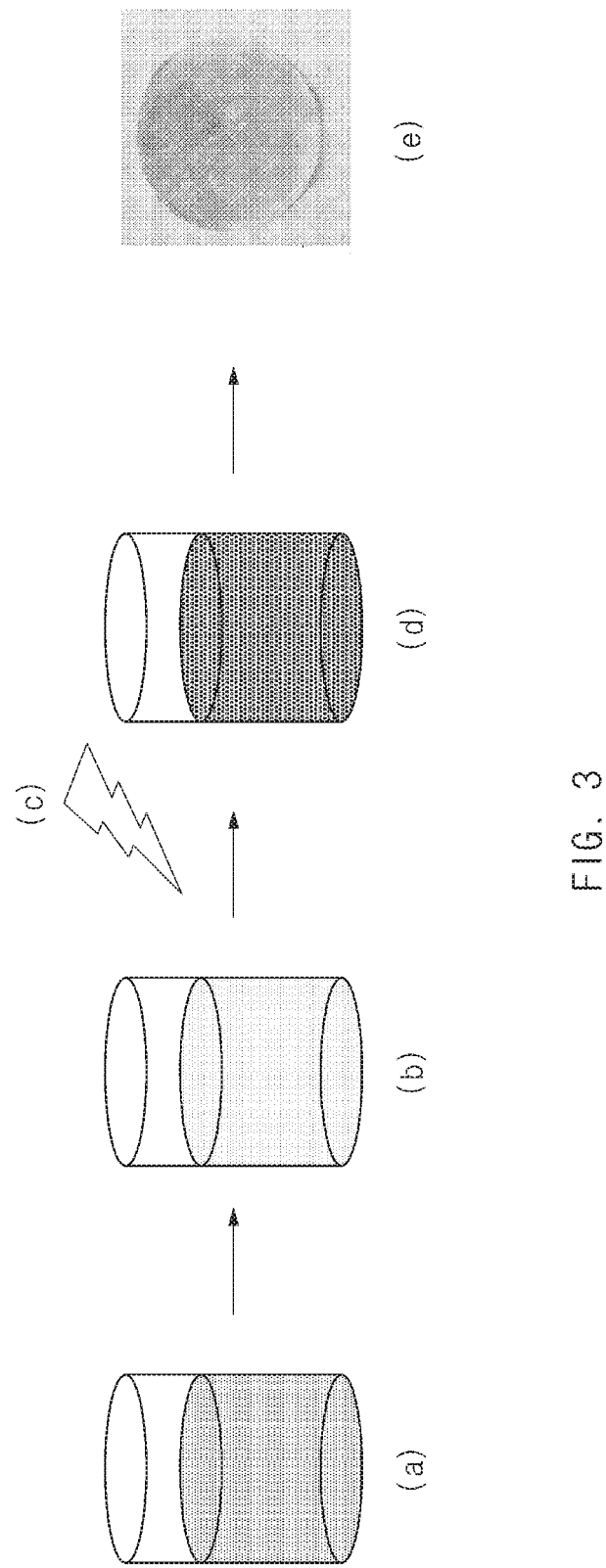
FIG. 3 illustrates an exemplary method for manufacturing an exemplary chemochromic nanoparticle with a core-shell structure comprising a hydrated or non-hydrated transition metal oxide according to an exemplary embodiment of the present invention.

FIG. 2 shows an exemplary method of preparing exemplary hydrated or non-hydrated transition metal oxide particles according to an exemplary embodiment of the present invention, and FIG. 3 show an exemplary method for manufacturing an exemplary chemochromic nanoparticle with a core-shell structure, which may include hydrated or non-hydrated transition metal oxide particles according to an exemplary embodiment of the present invention.

Preferably, the method may provide a method of preparing a tungsten oxide as shown in FIG. 2.

For example, the preparing of the hydrated or non-hydrated transition metal oxide may comprise: preparing an aqueous ammonium paratungstate solution (step (a)); adding hydrochloric acid to the aqueous ammonium paratungstate solution and stirring the mixture to prepare an aqueous tungstic acid solution (step (b) and step (c)); adding hydrogen peroxide to the aqueous tungstic acid solution to prepare an aqueous peroxo-polytungstic acid solution (step (d)); injecting the aqueous peroxo-polytungstic acid solution into an autoclave and performing primary heat treatment (step (e)); precipitating a hydrated tungsten oxide by air-cooling the autoclave after a reaction is terminated (step (f)); and obtaining the tungsten oxide (step (g)).

Preferably, the hydrated tungsten oxide may be represented with $WO_3$-$0.33H_2O$.

In the preparing of the hydrated or non-hydrated transition metal oxide, a concentration of the aqueous ammonium paratungstate solution of step (a) may be of about 1 wt % based on the total weight of the.

Further, in step (b) and step (c), a content ratio between tungsten and hydrochloric acid in the aqueous ammonium paratungstate solution may be of about 10:1 to 10:5. When the content ratio of hydrochloric acid is greater than about 5 or less than about 1, an ammonium group may not be appropriately separated, such that tungstic acid may not be easily formed.

In addition, a content ratio between tungsten and hydrogen peroxide in the aqueous tungstic acid solution of step (d) may be of about 10:1 to 10:5.

Further, the preparing of the hydrated or non-hydrated transition metal oxide may further include, after adding hydrogen peroxide, stirring the aqueous tungstic acid solution for about 60 minutes until the aqueous tungstic acid solution becomes transparent.

In addition, in the preparing of the hydrated or non-hydrated transition metal oxide, the primary heat treatment of step (a) may be performed at a temperature of about 160° C. for about 1.5 hours in an autoclave as an internal pressure inside the autoclave may be maintained at about 35 to 50 bar.

The water molecule-doped transition metal oxide may be the hydrated tungsten oxide ($WO_3$-$0.33H_2O$) and the hydrated tungsten oxide may be prepared by a hydrothermal synthesis reaction performed under high temperature and high pressure conditions as described above.

Further, in the method according to the present invention, a secondary heat treatment may be performed on the hydrated tungsten oxide obtained in step (g), such that non-hydrated tungsten oxide may be prepared (not illustrated).

In this case, the secondary heat treatment may be performed at a temperature of about 500° C. for about 2 hours after re-injecting the hydrated tungsten oxide into the autoclave.

As described above, according to the present invention, the hydrated or non-hydrated transition metal oxide may be formed at high productivity and a particle size thereof may range from about 1 to about 200 nm, when the hydrothermal synthesis method is used.

Further, as shown in FIG. 3, the method for manufacturing the chemochromic nanoparticle with a core-shell structure according to an exemplary embodiment of the present invention may be performed using a solution synthesis method including irradiating UV light. Hereinafter, the method for manufacturing chemochromic nanoparticles with a core-shell structure according to the present invention will be described.

For example, as shown in step (a) of FIG. 3, the metal catalyst precursor may be added to the organic solvent in which the polymer compound may be dissolved and subjected to sonication while being stirred for about 2 hours, thereby preparing the metal catalyst solution.

The metal catalyst precursor may include one metal or mixed particles of two or more metals selected from the group consisting of Pd, Pt, Ru, Mg, Au, and Ir. Preferably, the metal catalyst precursor may include one or a mixture of two or more selected from the group consisting of palladium chloride ($PdCl_2$), palladium ammonium nitrate ($Pd(NH_3)_2(NO_3)$), palladium bromide ($PdBr_2$), palladium oxide hydrate ($PdOH_2O$), palladium sulfate ($PdSO_4$), palladium nitrate ($Pd(NO_3)_2$), palladium acetylacetate (($CH_3COCH=C(O^-)CH_3)_3Pd$), platinum chloride ($PtCl_2$, $PtCl_4$), platinum bromide ($PtBr_2$), platinum oxide ($PtO_{2x}H_2O$), platinum sulfide ($PtS_2$), ruthenium oxide hydrate ($RuO_{2x}H_2O$), ruthenium acetylacetate [$((CH_3COCH=C(O^-)CH_3)_3Ru$], ruthenium bromide ($RuBr_3$), iridium chloride ($IrCl_3$), iridium acetylacetate (($CH_3COCH=C(O^-)CH_3)_3Ir$), and iridium chloride hydrate ($IrCl_{4x}H_2O$). In particular, the metal catalyst precursor may include palladium chloride ($PdCl_2$) containing palladium (Pd) metal particles, which may increase sensitivity in addition to significantly improving durability of a hydrogen sensor.

In addition, the polymer compound may be used as an adhesive and may improve compatibility between the transition metal oxide particles and the metal catalyst particles thereby improve coating efficiency. The polymer compound may include one or a mixture of two or more selected from the group consisting of polyurethane, polyetherurethane, cellulose acetate, cellulose acetate butyrate, cellulose acetate propionate, polymethylmethacrylate (PMMA), polymethylacrylate (PMA), polyacrylic copolymers, polyvinylacetate (PVAc), polyvinylacetate copolymers, polyvinylalcohol (PVA), polystyrene, polystyrene copolymers, polyethyleneoxide (PEO), polypropyleneoxide (PPO), polyethyleneoxide copolymers, polycarbonate (PC), polyvinylchloride (PVC), polycaprolactone, polyvinylpyrrolidone (PVP), polyvinylfluoride, polyvinylidene fluoride copolymers, and polyamide. Preferably, the polymer compound may be polyvinylpyrrolidone (PVP).

The organic solvent may be a polar solvent, such as an alcohol based solvent. Preferably, the organic solvent may be methanol or ethanol.

A mixed ratio (wt %) between the metal catalyst precursor, the polymer compound, and the organic solvent in the metal catalyst solvent may be about 1:1 to 2:2 to 3, or particularly about 1:1.5:2.5.

The polymer compound (PVP) may be used as a capping agent in the solution. For example, $Pd^{2+}$ ions, which are the metal catalyst, may be capped by the polymer compound (PVP), and as a result, the $Pd^{2+}$ ions may not be aggregated but may be easily dispersed in the solution as particles.

When the content ratio of the polymer compound is greater than about 2, since a large amount of $Pd^{2+}$ ions are capped, a size of Pd particles may be significantly decreased. As a result, nanoparticles having a predetermined size or greater may not be formed, such that a concentration of the metal catalyst solution may not be adjusted suitably in a subsequent reaction step. Further, when the content ratio of the polymer compound is less than about 1, since an amount of the polymer compound (PVP) capping the $Pd^{2+}$ ions is reduced, at least a portion of the Pd particles may have excessively increased sizes, and the other portion of the Pd particles may have excessively reduced sizes, such that the size of the Pd particles becomes significantly non-uniform. The result may be confirmed from the fact that a color of synthesized Pd may turn grey or white. Since coating efficiency between the transition metal oxide particles and the metal catalyst particles is deteriorated in the subsequent reaction step by the influence as described above and thus an amount of the metal catalyst particles coated on the surfaces of the transition metal oxide particles is decreased, capability of dissociating hydrogen atoms may be deteriorated.

As shown in step (b) of FIG. 3, the hydrated or non-hydrated transition metal oxide may be added to the prepared metal catalyst solution, thereby preparing the mixed solution.

The mixed ratio (wt %) between the metal catalyst precursor and the hydrated or non-hydrated transition metal oxide may be about 8:10 to 12.

When the mixed ratio (wt %) between the metal catalyst precursor and the hydrated or non-hydrated transition metal oxide is greater than about 8:12, the content of the core comprising the transition metal oxide in the finally manufactured chemochromic nanoparticle may be increased, but the content ratio of the shell comprising the metal catalyst may be decreased, such that responsibility for hydrogen gas may be decreased. Further, when the mixed ratio (wt %) between the metal catalyst precursor and the hydrated or non-hydrated transition metal oxide is less than about 8:10, the content of the core comprising the transition metal oxide in the finally manufactured chemochromic nanoparticle may be decreased, such that sufficient change in color may not be obtained.

As shown in step (c) and step (d) of FIG. 3, the chemochromic nanoparticles with a core-shell structure are manufactured by irradiating UV light to the mixed solution containing the metal catalyst precursor and the hydrated or non-hydrated transition metal oxide.

When the metal catalyst precursor and the transition metal oxide are mixed with each other, the color of the mixed solution may become light yellow, but when UV light is irradiated thereto, as the metal ions in the mixed solution may be dissociated, the mixed solution may be changed into an opaque grey solution. It may be appreciated from the change in color as described above that a synthesis reaction of the chemochromic nanoparticles is completed.

The irradiating of the UV light may be performed by exposure to UV light having a wavelength of about 365 nm and an output of about 1000 W at room temperature for about 2 to 3 minutes. When a UV irradiation time is within about 2 minutes, the Pd molecules may not be appropriately decomposed, and when the UV irradiation time is greater than about 3 minutes, a color of the separated Pd molecules may become excessively dark, such that a visual change in color for detecting hydrogen gas may not be suitably observed.

In addition, the thickness of the shell comprising the metal catalyst may be adjusted and controlled depending on the UV irradiation time and the concentration of the mixed solution. For example, the UV irradiation time may be suitably adjusted depending on the concentration of the mixed solution.

As described above, according to the present invention, the metal catalyst precursor, for example, $PdCl_2$ precursor may be separated into Pd molecule and $Cl_2$ by performing an eco-friendly UV photochemical method, that is, the UV irradiation process. The separated Pd molecule may react with the surface of the transition metal oxide particle, thereby forming the shell comprising the metal catalyst on the surface of the transition metal oxide particles in a dot form.

Subsequently, in the method according to the present invention, after the reaction is terminated, as shown in step (e) of FIG. 3, the mixed solution may be filtered and dried, such that the chemochromic nanoparticles with a core-shell structure may be obtained.

Further provided is a hydrogen sensor comprising the chemochromic nanoparticle manufactured by the method according to the present invention.

Moreover, the hydrogen sensor may be provided, and the hydrogen sensor may further selectively contain a polymer, aerogel, and a solvent. Further, in the hydrogen sensor according to the present invention, at the time of chemochromism due to exposure to hydrogen, a change in color in a visible light region may be significantly increased by injecting specific impurity molecules. For example, molecules having a large electronegativity such as —OH, —F, —Cl, or the like may be added to an original composition of the transition metal oxide to adjust a crystalline structure and an optical band gap.

In according to various exemplary embodiments of the present invention, the chemochromic nanoparticle with a core-shell structure manufactured by the method according to the present invention may be applied in various fields. For example, after the chemochromic nanoparticles may be combined with a polymer or aerogel to thereby be prepared as a coating agent, a dye, paint, or a pigment, and the coating agent, the dye, the paint, or the pigment may be used as a chemochromic hydrogen sensor. Alternatively, after the chemochromic nanoparticles with a core-shell structure are mixed with a suitable solvent to thereby be prepared as ink, and the ink is transferred/deposited on paper, a porous media substrate, or the like, may be used as a hydrogen sensor having excellent mechanical safety.

As described above, since the hydrogen sensor according to the present invention may be manufactured in a room temperature process, a manufacturing cost may be significantly decreased, and a production yield may be significantly increased. In addition, the hydrogen sensor may be applied to both an optical sensor and a chemochromism/discoloration type sensor, and it may be easy to form a large-area hydrogen sensor. Particularly, since the hydrogen sensor according to the present invention does not require a protective filter or passivation layer decreasing sensitivity or selectivity, which is applied to a surface of a hydrogen sensor according to the related art, deterioration of the sensitivity may be decreased, such that a detection limit concentration of hydrogen capable of being measured may be of about 1% or less, for example, of about 0.8% in the air.

Hereinabove, the present invention has been described in connection with various exemplary embodiments. However, various modifications can be made without departing from the scope of the present invention. Therefore, technical ideas of the present invention should not be limited to the exemplary embodiments described above but be defined by the appended claims and their equivalents.

EXAMPLE

Experimental Method and Equipment a. A color change reaction of 1% hydrogen (in 99% air balance gas ($N_2$, $H_2O$, $O_2$)) was observed under a mixed atmosphere of nitrogen, oxygen, and water vapor using an open chamber having an outlet.

b. All gasochromic tests were performed at room temperature, and a flow rate of 2 L/min was maintained on a sample.

Preparation Example 1: Preparation of Hydrated Tungsten Oxide

After preparing 1 wt % of an aqueous ammonium paratungstate solution by mixing ammonium paratungstate and water in a reactor, an aqueous tungsten solution was prepared by adding 1.5 ml of hydrochloric acid (HCl) thereto while stirring the aqueous solution, and additionally stirring the mixed solution for 30 minutes.

Then, 3 ml of hydrogen peroxide was added to the aqueous tungsten solution and stirred at room temperature for 60 minutes until the mixed solution became transparent, thereby preparing an aqueous peroxo-polytungstic acid solution.

The aqueous peroxo-polytungstic acid solution was injected into an autoclave in which an internal pressure of 35 to 50 bar was maintained, primary heat treatment was performed thereon at a temperature of 160° C. for about 1.5 hours.

After a reaction was terminated, the autoclave was air-cooled to room temperature and a precipitate was filtered, washed, and dried, thereby preparing water molecule-doped tungsten oxide ($WO_3$-$0.33H_2O$).

Preparation Example 2: Preparation of Non-hydrated Tungsten Oxide

The hydrated tungsten oxide prepared in Preparation Example 1 was re-injected into the autoclave and subjected to secondary heat treatment at a temperature of about 500° C. for 2 hours, thereby preparing non-hydrated tungsten oxide.

Example 1: Manufacturing of Nanoparticles for Hydrogen Sensor

Palladium chloride corresponding to a metal catalyst, polyvinylpyrrolidone corresponding to a polymer compound, and methanol corresponding to an organic solvent were injected into a reactor at a ratio of 1:1.5:2.5 (wt %) and subjected to sonication while being stirred for about 2 hours.

Subsequently, after the non-hydrated tungsten oxide of Preparation Example 2 was injected into the metal catalyst solution (metal catalyst precursor: transition metal oxide=8:10 (wt %)), the mixed solution was subjected to UV irradiation (wavelength: 365 nm, output: 1000 W) within about 2 minutes while being stirred.

When a color of a reaction mixture solution was changed from light yellow to opaque grey, the reaction was terminated, and a precipitate was filtered and dried, thereby manufacturing chemochromic nanoparticles with a core-shell structure.

Example 2: Manufacturing of Nanoparticles for Hydrogen Sensor

Chemochromic nanoparticles with a core-shell structure were manufactured by the same method as in Example 1 except for using the hydrated tungsten oxide of Preparation Example 1 instead of the non-hydrated tungsten oxide of Preparation Example 2.

Experimental Example

Experimental Example 1: Hydrogen Gasochromic Test

A color change reaction to hydrogen gas was observed with the naked eyes while passing the chemochromic nanoparticles manufactured in Examples 1 and 2 through 1% hydrogen gas (containing 99% of nitrogen) under the air atmosphere in which nitrogen, oxygen, and water vapor were mixed with each other in an intact state in which the chemochromic nanoparticles were obtained from a filter paper.

As a result, as shown in FIG. 4, the chemochromic nanoparticles with a core-shell structure containing the non-hydrated transition metal oxide of Example 1 had a turbid green color before exposure to hydrogen gas, but after exposure to hydrogen gas, the color of the chemochromic nanoparticles was changed to deep green, such that hydrogen gas may be detected.

Further, as shown in FIG. 5, the chemochromic nanoparticles with a core-shell structure containing the hydrated transition metal oxide of Example 2 had an almost pale yellow color before exposure to hydrogen gas, but after exposure to hydrogen gas, the color of the chemochromic nanoparticles was changed to deep blue, such that hydrogen gas may be detected.

Experimental Example 2: Voltage-Current Response of Hydrogen Sensor

After preparing inks by mixing the chemochromic nanoparticles manufactured in Examples 1 and 2 with a solvent, the inks were transferred on paper or a porous media substrate, thereby manufacturing hydrogen sensors.

Then, voltage-current responses with respect to the hydrogen sensors were measured, and as a result, it was confirmed that in the sensor containing the chemochromic nanoparticles of Example 1, a current was increased 100,000 times in a range of −10V to 10V as illustrated in FIG. 6. That is, it was observed that after exposure to hydrogen gas, the current was increased than that before exposure to hydrogen gas.

Further, it was confirmed that in the sensor containing the chemochromic nanoparticles of Example 2, a current was increased 10 times in a range of −10V to 10V as illustrated in FIG. 7. That is, it was observed that after exposure to hydrogen gas, the current was increased than that before exposure to hydrogen gas. These changes indicate sensitivity of the hydrogen sensor according to the present invention to hydrogen gas.

Particularly, as shown in the result, since in the sensor of Example 1, a change in color was small, but the current was significantly increased, the sensor of Example 1 may be excellent as a material of a resistance type sensor, and since in the sensor of Example 2, an increase in current was small, but the change in color was significant, the sensor of Example 2 may be suitably used in a chemochromic application field.

As described above, according to the exemplary embodiments of the present invention, the hydrogen sensor of which hydrogen gas detection efficiency characteristics are improved due to a specific surface area significantly increased by containing the chemochromic nanoparticles with a core-shell structure in which the metal catalyst layer is partially coated on the surface of the hydrated or non-hydrated transition metal oxide, manufactured by an eco-friendly UV photochemical method may be manufactured.

Hereinabove, although the present invention has been described with reference to exemplary embodiments and the accompanying drawings, the present invention is not limited thereto, but may be variously modified and altered by those skilled in the art to which the present invention pertains without departing from the spirit and scope of the present invention claimed in the following claims.

What is claimed is:

1. A method for manufacturing a chemochromic nanoparticle, the method comprising:
preparing a hydrated or non-hydrated transition metal oxide;
preparing a metal catalyst solution by dissolving a metal catalyst precursor and a polymer compound in an organic solvent;
preparing a mixed solution by adding the hydrated or non-hydrated transition metal oxide to the metal catalyst solution;
manufacturing the chemochromic nanoparticle with a core-shell structure by irradiating the mixed solution with UV light; and
obtaining the chemochromic nanoparticle by filtering the mixed solution, wherein the ratio between the metal catalyst precursor and the hydrated or non-hydrated transition metal oxide in the mixed solution is 8:10 to 8:12 by weight.

2. The method according to claim 1, wherein the polymer compound comprises one or a mixture of two or more selected from the group consisting of polyurethane, polyetherurethane, cellulose acetate, cellulose acetate butyrate, cellulose acetate propionate, polymethylmethacrylate (PMMA), polymethylacrylate (PMA), polyacrylic copolymers, polyvinylacetate (PVAc), polyvinylacetate copolymers, polyvinylalcohol (PVA), polystyrene, polystyrene copolymers, polyethyleneoxide (PEO), polypropyleneoxide (PPO), polyethyleneoxide copolymers, polycarbonate (PC), polyvinylchloride (PVC), polycaprolactone, polyvinylpyrrolidone (PVP), polyvinylfluoride, polyvinylidene fluoride copolymers, and polyamide.

3. The method according to claim 1, wherein the organic solvent comprises an alcohol based solvent.

4. The method according to claim 1, wherein the irradiating of the mixed solution is performed by exposure of the mixed solution to the UV light for about 2 to 3 minutes at room temperature, wherein the UV light has a wavelength of 365 nm and is from a 1000 W source.

* * * * *